United States Patent [19]
Härle

[11] Patent Number: 5,643,269
[45] Date of Patent: Jul. 1, 1997

[54] EXTERNALLY THREADED BODIES FOR USE AS TAPS OR SCREWS

[76] Inventor: Anton Härle, Drechslerweg 40, 48161 Münster, Germany

[21] Appl. No.: 308,119

[22] Filed: Sep. 16, 1994

Related U.S. Application Data

[63] Continuation-in-part of Ser. No. 32,453, Mar. 17, 1993, abandoned, which is a continuation of Ser. No. 749,524, Aug. 26, 1991, abandoned.

[30] Foreign Application Priority Data

Aug. 24, 1993 [DE] Germany .................. 40 26 777C2

[51] Int. Cl.$^6$ .................................. A61B 17/00
[52] U.S. Cl. .................. 606/79; 606/72; 606/73
[58] Field of Search .................. 606/80, 72–79; 408/222, 219; 470/198

[56] References Cited

U.S. PATENT DOCUMENTS

| | | | |
|---|---|---|---|
| 177,731 | 5/1876 | Martin | 408/222 |
| 1,693,768 | 12/1928 | Steinrock | 408/219 |
| 2,479,730 | 8/1949 | Dewar | 408/219 |
| 4,181,457 | 1/1980 | Holmes | 408/219 |

*Primary Examiner*—Michael A. Brown

[57] ABSTRACT

There is provided set of at least two externally threaded bodies each of which has a cylindrical external surface provided with a screw thread. The screw threads have identical pitches, and the crest diameter or diameters of one or more helices of one of the screw threads is or are larger than the crest diameters of helices of the other screw thread. The externally threaded bodies can constitute screws or taps for use in osteosynthesis. If a screw becomes loose, it is removed and the hole for such screw is tapped with a larger tap prior to insertion of a screw having helices with crest diameters larger than the crest diameters of helices of the removed screw. The core diameters of the screw threads of a set of externally threaded bodies need not be the same.

24 Claims, 3 Drawing Sheets

EXTERNALLY THREADED BODIES FOR USE AS TAPS OR SCREWS

CROSS-REFERENCE TO RELATED APPLICATIONS

This application is a continuation-in-part of Ser. No. 08/032,453 filed Mar. 17, 1993, now abandoned which, in turn, is a continuation of Ser. No. 07/749,524 filed Aug. 26, 1991, now abandoned.

BACKGROUND OF THE INVENTION

The invention relates to improvements in taps, screws and analogous externally threaded bodies. Externally threaded bodies are characterized by projecting helical ribs winding around a cylindrical or conical shaft. The sizing of externally threaded bodies is based on the major diameter of the threaded portion which stands in certain relationship with the pitch of the thread.

Taps being used to cut an internal thread are available in different types, for example as machine-screw taps and hand taps. One subgroup of the latter are the serial hand taps which are normally sold in sets of two or three taps numbered, respectively, 1, 2, 3 with one, two, or three rings, respectively, on the shank. The No. 1 tap, called rougher, makes the roughing cut and is smaller both in major and pitch diameter. The No. 2 tap, called intermediate, cuts a somewhat fuller thread, and the No. 3 tap, called finisher, finishes the thread. In these sets of the serial hand taps each tap of set must be used in order to manufacture a finished threading, and all taps in the set belong to the same size.

It is well known to use screws or similar fasteners as a means for securing bars, rods, plates or other reinforcing, stiffening, immobilizing or aligning parts to broken or weak bones. Physicians specializing in the field of osteosynthesis employ such plates, bars, rods or like parts to ensure that the healing of a bone fracture will take place under optimal circumstances. This necessitates reliable attachment of plates or like parts (hereinafter referred to as plates) to the damaged bones, normally by means of so-called bone screws. The screws must be driven into a bone without any play to ensure that the plate that is being affixed thereby will maintain the joined fragments of a bone or two or more interconnected bones in optimum positions for rapid healing, i.e., in an optimum orientation of bones and/or bone fragments relative to each other.

As a rule, a plate that is to be implanted into the body of a patient and is to be secured to a tubular bone is provided with properly distributed holes for the passage of bone screws. The shanks of the screws are driven into the bone to locate one side of the plate adjacent the bone that is to be stabilized, reinforced or immobilized, and the heads of the screws are caused to bear against the opposite side of the plate. Those ends of the holes that are adjacent the opposite side of the plate are often configured in such a way that they receive portions of or the entire heads of the respective screws. A pattern can be used to drill holes into selected portions of a bone by resorting to a bone drill, and the surfaces surrounding the thus formed holes are provided with threads by resorting to a bone tap. Reference may be had, for example, to U.S. Pat. No. 4,943,292 granted Jul. 24, 1990 to Foux. The strength of the connection between the shank of a bone screw and a bone depends upon the relationship of dimensions of the screw thread on the tap and the dimensions of the screw threads of the bone screws.

The major part of the retaining action is furnished by the cortex or outer layer of the bone. Very little retention can be expected from the spongiosa and/or the tissue lining the marrow cavity. As a rule, a conventional screw that is driven into a tubular bone is subjected primarily or exclusively to tensional (pulling) stresses. In other words, care should be taken to ensure that such stresses do not result in extraction of the shank of a bone screw from the tapped hole in the bone. By far the major part of the retaining action is lost if the external thread is not a tight fit in the tapped hole of the bone. Attempts to eliminate such problems include the utilization of relatively long bone screws which are caused to pass all the way through a bone and mate with nuts on that side of the bone which faces away from the plate.

The problems are even more serious when a plate is to be affixed to one or more vertebrae, i.e., when one or more bone screws must be driven into the vertebra or vertebrae. Due to the anatomy of the spinal column, only one screw can be driven into a vertebra. On the other hand, a screw which is driven into a vertebra must often carry a very substantial load because the entire weight, or nearly the entire weight, of the upper part of the body must be borne by such screw. This creates problems, especially if a vertebra must be fixed in position with a very high degree of reliability, for example, in order to ensure desirable consolidation of the damaged spinal column. The situation is aggravated because the shank of the screw can be driven only into a certain portion of a vertebra, namely into the cortical parts of the pedicles because the remaining parts of the vertebra do not exert a pronounced retaining action. Reference may be had to German patent application No. 36 39 522 of Mattheck et al. (published Jun. 1, 1988). As mentioned above, a screw that is driven into a tubular bone (e.g., tibia) in an extremity of an animal body can be anchored in two cortices if it extends all the way through the bone. On the other hand a screw that is driven into a vertebra is anchored only once, namely in the narrow basal part called pedicle between the neural arch and the front part of the vertebra. The shape of a pedicle in sagittal section is that of a spool, and the shank of a screw can be reliably anchored only in the narrow central portion of such "spool" wherein the screw is capable of establishing and maintaining a satisfactory direct transmission of force as a result of tangential contact with the cortex of the respective portion of the vertebra.

A frontal cross-section through a pedicle has an elongated oval outline and can vary from one side of the vertebra to the other. This further complicates the insertion of a bone screw. Satisfactory fixation of a screw in a vertebra is a very difficult and complex procedure and is successful only when the external thread of the screw is in direct contact with the cortex of the pedicle in the region of the isthmus.

Still further, it is difficult, if not impossible, to invariably and reliably determine the maximum-diameter locus for the making of a tapped bore in a vertebra; this creates additional problems in connection with the selection of optimal bone drills, bone taps and bone screws. If, for example, the diameter of the initially chosen screw is too small there is no possibility to switch to a bone screw having a larger diameter without damaging the internal thread. As a rule, in externally threaded bodies the pitch is increasing together with the major diameter; screws for use as a tight fit in internal threads, i.e., without any play, as for example for use in wood, plastic and bones normally have a close relationship of major diameter and pitch. FIG. 6 shows portions of three conventional taps for the making of threadings with different major diameters C1, C2, C3; due to the fact that the ascending flanks of all threads exhibit the same angle gamma in relationship to the axis of the thread, the pitches h1, h2, h3 increase parallel to the major diameter. Consequently the threadings do not fit into each other anymore. For example, if such three taps are used one after the other to create an internal threading in a bore, the finally produced internal thread will have an irregular thread contour. In FIG. 7 a cross-section of such an irregular conventional internal threading containing a screw is displayed; there are many portions (blank areas) between the threadings in which the screw is not in direct contact with the internal thread. In addition, the internal threading has changed somewhat to an irregular hole; furthermore, this weakens the extraction resistance of the internal thread. If someone, to avoid the need to ultimately switch to a larger sized screw, initially selects a screw having an excessive diameter, such person will eventually face more severe problems due to the anatomical conditions around the neural arch when she or he penetrates the spinal foramen. Since the spinal cord and the roots of the nerves are immediately adjacent the pedicle of a vertebra, the shank of a screw that is driven into the vertebra may not extend from the isthmus of the pedicle.

Another factor that must be taken into consideration is that the frontal diameter of a pedicle varies within a rather wide range. In each segment of the spinal column, the difference between the maximal and minimal values can be as large as 6 mm. On the other hand, reliable and stable anchoring of the shank of a bone screw is conditioned upon proper selection of the dimensions of the tap and of the shank of the bone screw. If the dimensions of the shank of the bone screw are too small, the connection between the screw and the bone is unstable and the position of the implanted plate is not determined with the required degree of accuracy. Furthermore, too small screws are at risk of breakage, which is a very severe problem with bone screws of prior art in spinal fixation. If the dimensions of the screw are excessive, this often leads to neurological complications and can even result in paralysis. The invention relates to repair mechanisms for internal threadings which are worn out or are damaged by corrosion during use or have irregular flank profiles for other reasons, such as for example due to improper tapping. In accordance with the teachings of prior art, damaged internal threadings are treated in such a way that a new bore is drilled with a diameter being at least a little larger than the original major diameter of the internal threading in order to eliminate the damaged flanks of the old female threading. Thereafter, the enlarged bore is tapped to create a new internal threading which has a minor diameter larger than the original major diameter. The original screw fastener to be engaged in these new internal threadings has to be replaced too by one of larger size. In the cases where such a larger screw fastener is not acceptable, the so-called insert technique is applied, for example, by resorting to wire inserts of the type disclosed in U.S. Pat. No. 4,459,248. This insert technique does not eliminate the problems arising from the larger sized bore in material with internal threading. When the major diameter of the internal thread is enlarged by about 20 to 30 percent to be engaged by the insert, the remaining material around the internally threaded bore may be reduced to such an extent that as a result the holding power is seriously impaired; in critical cases the entire material block which holds these internal threadings has to be replaced.

OBJECTS OF THE INVENTION

An object of the invention is to provide a novel and improved set or group of externally threaded bodies which can be utilized in the field of osteosynthesis as well as in certain other fields to ensure reliable and long-lasting retention of screws (such as bone screws) or analogous parts in tapped holes or bores in many materials.

Another object of the invention is to provide a novel and improved set of bone taps.

A further object of the invention is to provide a novel and improved set of bone screws.

Still another object of the invention is to provide novel and improved matching pairs of tapping bodies and screws, particularly for use in osteosynthesis.

A further object of the invention is to provide novel and improved designs of external threads on shanks of screws and tapping bodies.

An additional object of the invention is to provide a novel and improved method of anchoring screws in bones of all kinds including tubular bones and vertebrae.

Another object of the invention is to provide a novel and improved method of investigating and determining the optimal screw diameter by sensing the resistance which a tap offers to penetration into a drilled hole or into a previously tapped hole in a bone.

A further object of the invention is to provide a novel and improved method of ascertaining when a screw thread penetrates into the cortical region of a bone.

An additional object of the invention is to provide a novel and improved method of compensating for loosening of a screw in a tapped bore or hole.

Another object of the invention is to provide a novel and improved method of repairing worn out or otherwise damaged internal threadings with minimal enlargement of major diameter of the internal threading.

SUMMARY OF THE INVENTION

The invention relates to sets of externally threaded bodies that differ in the major and/or minor diameter but have the same pitch and, in the case of taps or tapping bodies, each tap or tapping body is the set will produce a finished threading. These sets of externally threaded bodies can be used in all procedures and materials where externally threaded fasteners are used, particularly in wood, plastic, metallic and analogous materials. More particularly, the inventon relates to improvements in externally threaded bodies that can be used with advantage to form threads in bones as well as to secure parts (e.g., implantable plates) to bones which are provided with tapped bores or holes.

One feature of the present invention resides in the provision of a set of at least two externally threaded bodies each of which can constitute a screw or a tapping body, more particularly a bone screw or a bone tap. Each body has an at least partly cylindrical external surface provided with a screw thread. The screw threads of the at least two externally threaded bodies have identical pitches and such threads have helices with crest diameters which are selected in such a way that the crest diameter of one of the screw threads is greater than the crest diameters of helices of the other screw thread. The screw threads of the at least two externally threaded bodies can have different root diameters.

If the screw threads of different crest diameters are superimposed, a line through the crests of the different threads is a bisecting line of the threads and flank angles. A crest diameter of the at least one helix of the thread preferably exceeds the crest diameter of the helix or helices of the other thread or threads by at least 0.05 mm. At least one other helix of the one thread can have a crest diameter which equals or approximates the crest diameters of helices of the other thread, and the one screw thread can have additional other helices which follow the at least one other helix and have crest diameters larger than the crest diameter of the at least one other thread. The core diameter of the thread of at least one of the externally threaded bodies can increase in the axial direction of the respective body.

If the at least two externally threaded bodies of the set are bone taps, a second set can comprise at least two bone screws each of which has an at least partly cylindrical external surface with a screw thread. The screw threads of the bone screws have identical pitches and the crest diameter of at least one helix of the screw thread on one of the bone screws is larger than the crest diameters of helices forming part of the screw thread of the other bone screw. The root diameters of screw threads on the bone screws can exceed the root diameters of screw threads on the bone taps by 0.05–0.2 mm, and the crest diameters of screw threads on the screws can exceed the crest diameters of screw threads on the bone taps by 0.05–0.2 mm.

The number of helices forming part of the screw thread on one externally threaded body of a set can match the number of helices of the screw thread on the other externally threaded body of the same set.

According to the invention, worn out or otherwise damaged internal threadings can be repaired with minimal enlargement of the major diameter of the internal threading to create a new regular and smoothly working threading having the same holding power as the original one. If a small reduction of holding power is acceptable, such repair can be completed even without any enlargement of the major diameter of the internal threading. The screw fastener to be engaged in this repaired internal threading has only a negligibly increased major diameter in the first instance and will be of same major diameter in the latter case.

The first suggested procedure comprises that the original internal threading be tapped by a tapping body of a set according to the invention. If this original internal threading is worn out or damaged for other reasons, the person in charge will use a tapping body with next higher number of this set having crest and root diameters being an incremental step larger than the firstly used tapping body and tap a new internal thread with complete regular thread flanks and thread configuration which will be about two to five percent larger in major diameter than the original internal threading. Then the person in charge will engage this new internal threading by a corresponding screw fastener which has the appropriate size, i.e., the same number of the corresponding set of screw fasteners.

In cases where excessive working load, applied to the internal threading, was the cause for damage to the internal threading, the load bearing capacity of the internal threading can be increased according to the invention with minimal enlargement of the major diameter of the internal thread. In such a repair procedure, only the major diameter will be increased with no or a smaller increase of the minor diameter in comparison to the major diameter. For this purpose, besides the increase of the major diameter the flank angle of the tapping body will decrease so that the new thread exhibits a greater height of thread in comparison to the original one.

If the major diameter may not be enlarged during the repair of the damaged internal threading, according to invention the tapping body for the repair will have either an increased core diameter with constant crest diameter in comparison to the original tapping body, or solely or in addition the flank angle of the tapping body for the repair will be increased in comparison to the original tapping body.

Depending upon the special needs in a particular situation, the invention offers several novel and improved procedures to repair damaged internal threads and, in addition if there is a need to increase the holding power, without any or with only minimal enlargement of the major diameter of the internal threading.

Another feature of the invention resides in the provision of at least one thread cutting tool that can be used to cut, roll and/or otherwise shape the screw threads of the sets of screws and/or tapping bodies.

The novel features which are considered as characteristic of the invention are set forth in particular in the appended claims. The improved sets of screws and/or tapping bodies themselves, however, both as to their construction, configuration and mode of utilization, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
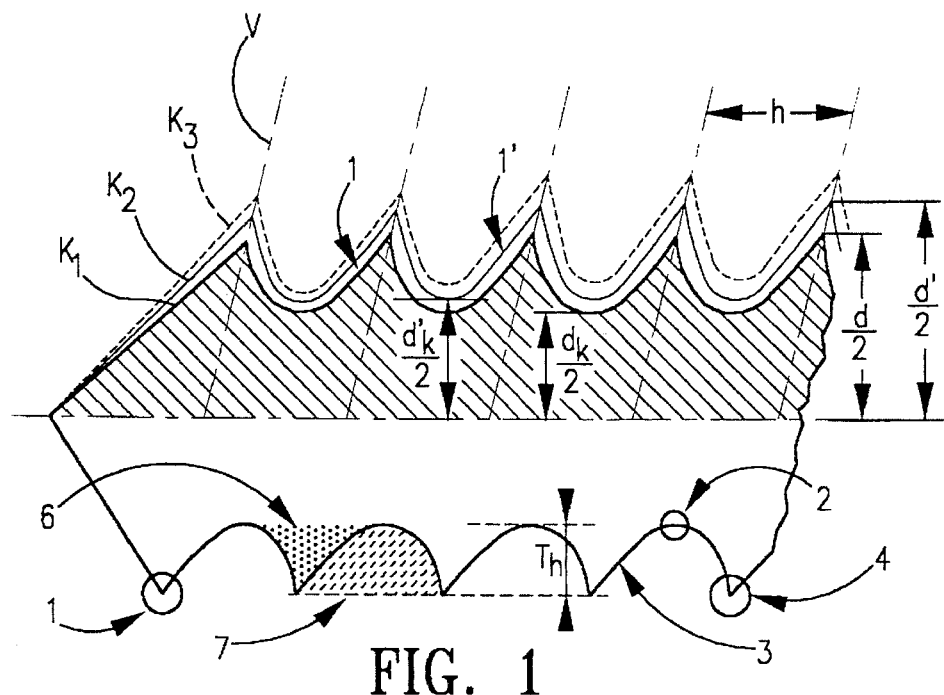
FIG. 1 shows a set of two externally threaded bodies having screw threads which are dimensioned and shaped in accordance with one presently preferred embodiment of the invention.

FIG. 1 shows portions of two externally threaded bodies 1 and 1' having cylindrical external surfaces provided with non-identical screw threads K1 and K2. The pitch h of the screw thread K1 is the same as that of the screw thread K2; however, the crest diameters d of the helices of the thread K1 are smaller than the crest diameters d' of the helices of the thread K2. Moreover, the root diameter dk of the thread K1 is smaller than the root diameter dk' of thread K2. A portion of the screw thread of a third externally threaded body is indicated in the drawing by a broken line K3. The pitch h of the thread K3 is the same as that of the screw thread K1 or K2. The crests of the helices of the threads K1, K2 and K3 are sharply defined. The phantom lines V through the crests of all three threads are bisecting lines or medians of the threads in that they divide the flank angles at the crests of the respective helices into halves.

If the externally threaded bodies 1 and 1' are bone taps, the internal threads which are cut with the screw thread K1 are not damaged or destroyed when the same bore is thereupon provided with an internal thread by using the externally threaded body 1'. The same holds true if the tapping with the body 1' is followed by tapping with the externally threaded body having the screw thread K3.

Analogously, if the externally threaded bodies are screws, the screw 1 will be a tight fit in a bore which has been tapped with a tap having the screw thread K1, and the screw 1' will be a tight fit in a bore which has been tapped with a tap having the screw thread K2.

All crest diameters d of the screw thread K1 need not be smaller than the crest diameters d'; for example, one or more left-hand crest diameters d', e.g., in the threaded start portion of the screw thread K2, can approximate or match the crest diameters d of the threaded main portion and the remaining crest diameters d' can be larger than the crest diameters d. The differences between the diameters of cylindrical surfaces into which the screw threads K1 and K2 are cut can be 0.05 mm or more.

The root diameter dk or dk' need not be constant, i.e., each of these root diameters can increase in a direction from the tip toward the other end of the respective externally threaded body. The increase of the root diameters dk and/or dk' can be disproportionate.

The difference between the crest diameter d and d' of helices of screw threads of taps and corresponding screws can be in the range of 0.5 to 2 mm, the same as the difference between the root diameters dk and dk'.

The improved set of taps or screws can be used in osteosynthesis as well as in numerous other fields, particularly in fields where screws are to be inserted into tapped bores or holes made in wood, plastic or a relatively soft metallic material.

An important feature of the improved set of screws and taps is that the pitches h of their screw threads K1, K2, K3 are the same even though their root diameters and/or crest diameters are different. This brings about the afore discussed advantage that a bore which has been tapped with a smaller tap (e.g., a tap having the screw thread K1 or K2) can thereafter be tapped with a larger tap (e.g., the one having the screw thread K2 or K3) without damaging the existing internal thread in a bone or in another part that is to receive a screw having a thread K1, K2 or K3 provided all the used taps and/or all screws belong to the same set of externally threaded bodies. The person in charge of tapping a bore or hole in a bone can sense the resistance that a tap offers to penetration into a drilled hole or into a previously tapped hole, i.e., the person in charge can sense when the screw thread K1, K2 or K3 penetrates into the cortical region of the bone or particularly the pedicular isthmus (shown in FIG. 5, 25 at 12. Thus, all such person has to do is to cut threads with progressively larger taps until she or he ascertains that the tap is firmly anchored in the cortex, e.g., in the cortex of a pedicle, which normally has an oval shape in frontal cross-section.

Figure 4:
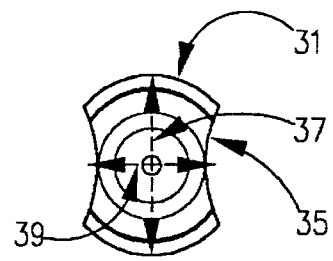
FIG. 4 is an end elevational view of a bone tap for cutting internal threads into a bone hole.

If a tap is used with a major (37) and minor (39) diameter (see FIG. 4), the person in charge feels during tapping when the resistance the tap offers is even during a total turn of the tap; in this case the major diameter of the tap is turning in the soft cancellous bone. On the other hand, if a tap with major and minor diameters offers different resistances during a total turn of the tap, the person in charge realizes by such uneven resistances during turning the tap that the major diameter is cutting the thread into the cortical region of the pedicle. The number of that tap indicates the size of the appropriate screw with the maximum diameter possible in this individual case. The tap is thereupon withdrawn and such withdrawal is followed by insertion of a corresponding bone screw. Thus, the set of externally threaded bodies with the aforesaid features enables the person in charge to determine the maximum diameter a screw can have in a particular pedicle. This measurement of the maximal possible screw was up to now impossible to determine during surgery. Since the screw breakage due to underdimensioned screws is a serious problem in spinal surgery, the set of taps and/or screws is of great advantage to the spinal surgeon and to the patients.

If an inserted screw becomes loose after a certain period of use, it is withdrawn and the thus exposed hole is thereupon ready to receive a tap having the next-larger thread (such as K2 or K3). The tapping operation is followed by inserting a screw having a corresponding thread K2 or K3. Thus, one and the same hole can receive a series of screws having progressively larger diameters without any damage to the internal threads. If the differences between the crest diameters of screws in a set are sufficiently small, the loose screw can be replaced directly by the next larger screw without a second tapping. This procedure is novel and allows to repair a loosened or damaged internal thread with minimal enlargement of the threaded bore; Heretofore, such a repair necessitated the drilling into the damaged internally threaded hole a new bore with a core diameter which equals or exceeds the crest diameter of the old thread. In many applications, and especially in osteosynthesis, such a procedure encounters a lot of problems and often is impossible due to the anatomical conditions.

It is clear that each set of taps and/or screws can consist of three, four or more discrete externally threaded bodies, as long as the pitches h of screw threads of bodies in each set are the same and as long as one of the diameters or flank angle of at least one helix of the screw thread of one body in a set differs from the corresponding or flank angle of the helices of the screw thread of each other body in the same set of screws or taps.

Figure 2:
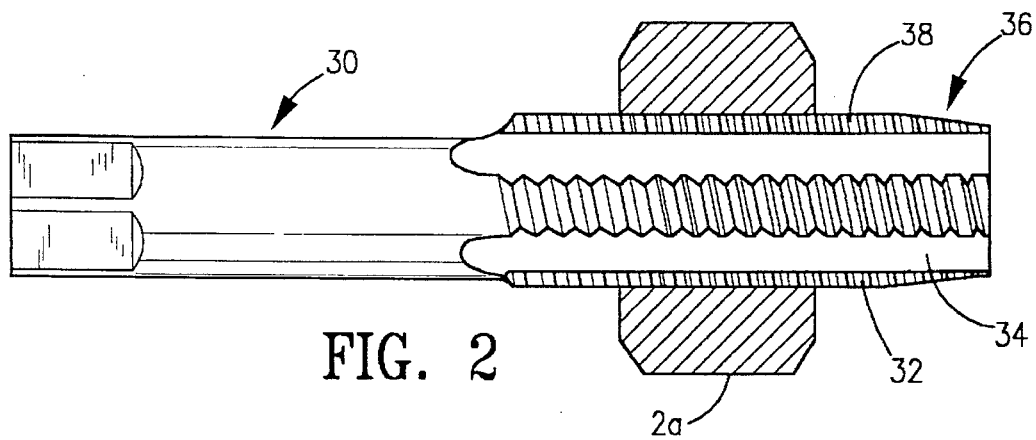
FIG. 2 is a partly elevational and partly sectional view of a tool for cutting threads of the type shown in FIG. 1.
Figure 3:
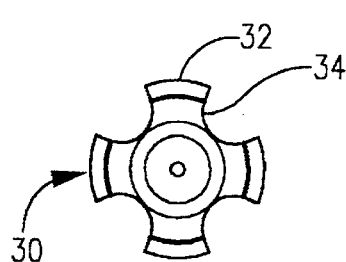
FIG. 3 is an end elevational view of the tool.

The tools of FIGS. 2 and 3 can be used to cut threads of the type shown in FIG. 1. The tool 30 of FIGS. 2 and 3 comprises longitudinally extending ribs 32 which are separated by longitudinally extending grooves 34. One end of the tool 30 has an inserting section 36 followed by a working section with cutting teeth 38 serving to cut the threads K.

In another embodiment (FIG. 4), the tool sections 36 and 38 have only two longitudinally extending ribs 31 which are separated by two grooves 35; as a result of this reduction of ribs and grooves the tap has now a major diameter 37 and a minor diameter 39. This feature of having a major and a minor diameter enables the tap to give notice when the major diameter is entering the cortical region of the oval shaped pedicle.

Thus, and as pointed out previously, the person in charge can determine the maximum crest diameter of the thread and select a suitable screw for the insertion into the pedicle. The set of taps with these features becomes a novel instrumental equipment for measurement of the diameters of the pedicles and for selection of sizes of screws.

Figure 5:
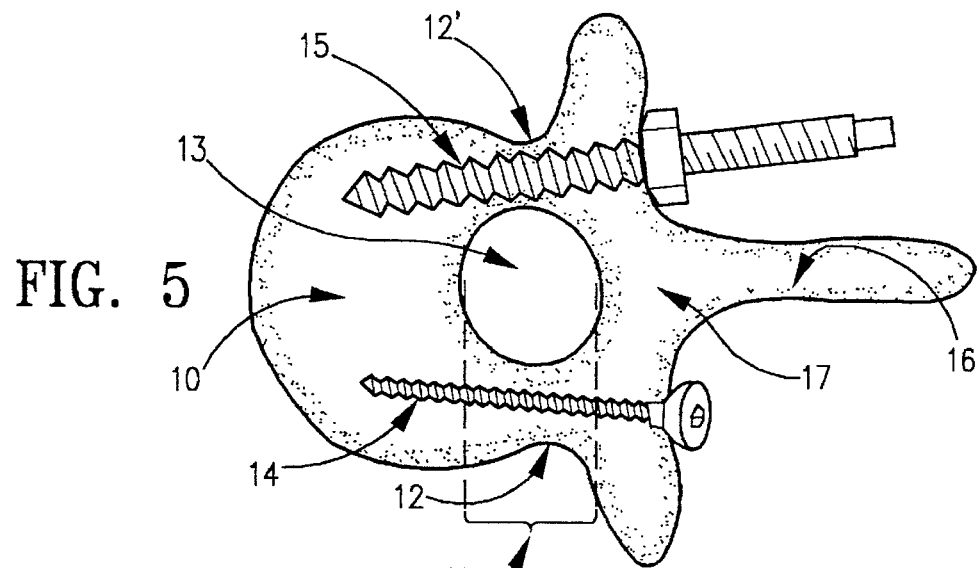
FIG. 5 is a cross-sectional view of a vertebra with two screws inserted through the pedicles.

FIG. 5 presents a sagittal cross-section through a vertebra with a vertebral body 10 and the spool shaped pedicle area 11 which contains the isthmic narrowness 12. Between the two pedicles 12 and 12' the neural foramen 13 is located which contains the spinal cord and the nerves. In the vertebra, the cortical areas 16 with harder bone are dotted whereas the areas with soft cancellous bone 17 are blank. A conventional bone screw 14 is inserted from the dorsal part of the vertebra through the lower pedicle 12 into the vertebral body 10. The bone screw 14 with a crest diameter smaller than the isthmic narrowness in the pedicle 12 has no contact with the cortical bone and therefore exhibits only minor holding and fixation power. Through the upper pedicle an ideal-sized pedicle screw 15 is inserted, where the threaded surface of the screw is in tight contact with cortical bone in the pedicle area into which a female threading is cut. Due to the suitable size and the insertion into an internally threaded cortical part of the pedicle, the fixation and holding power of the screw 15 are superior to those of the screw 14. In addition, due to the thicker core diameter of the screw 15 which exhibits the maximum diameter of suitable screw for insertion into the pedicle, the risk of screw breakage due to overload is decreased in screw 15.

Figure 6:
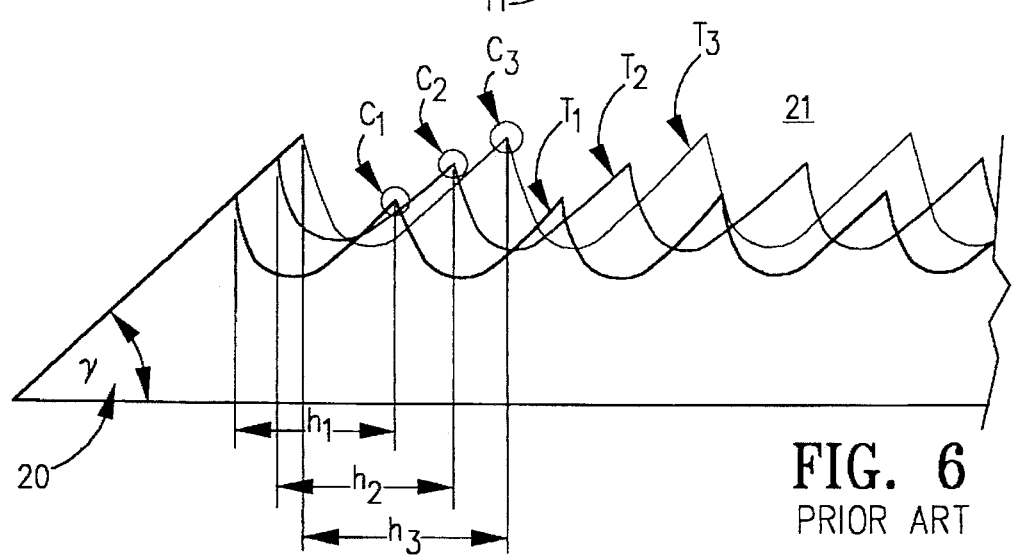
FIG. 6 illustrates in cross-section the internal thread contour when three conventional taps or screws with different crest diameters and different pitches are inserted seriatim into a bore.

FIG. 6 shows three superimposed thread contours T1, T2, T3 with different crest diameters C1, C2, C3. Due to the thread standards of prior art concerning the relationship of major diameter, thread pitch and the constant angle gamma 20 at the ascending flank, the threads have together with increasing crest diameters also increasing pitches h1, h2, h3. When such taps are used in series with increasing crest diameters, i.e., firstly T1 with pitch h1 followed by T2 with h2, then the first threading cut by T1 will be damaged due to the difference in the pitches. If three of such standard taps of prior art are used one after the other, i.e., firstly T1, then T2 and thirdly T3, the thread that was originally cut by T1 will be seriously damaged.

Figure 7:
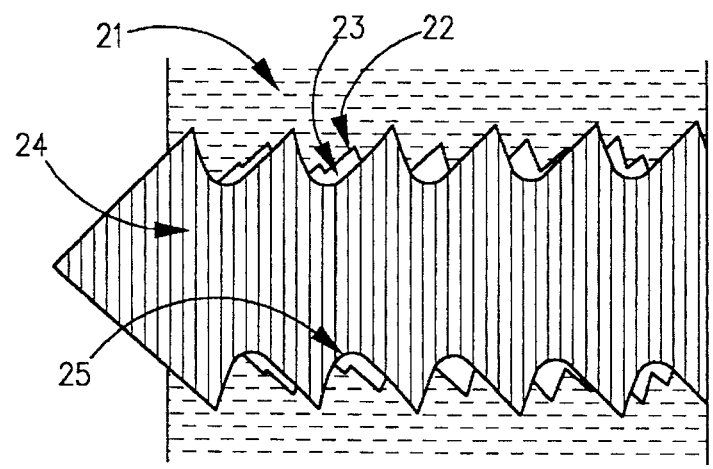
FIG. 7 shows a section through an internal threading according to FIG. 6 with a screw inserted.

FIG. 7 shows a longitudinal section through a block 21 with such an internal threading 22 into which a screw 24 with thread contours T3 is inserted. It can be seen that there are a lot of regions 23 where the threaded surface 25 of the screw 24 is not in direct contact with the contour of the irregularly contoured internal threading 22. These contact lacking region or areas 23 severely reduce the holding power and extraction resistance of a screw 24 that is inserted into the block 21.

Figure 8:
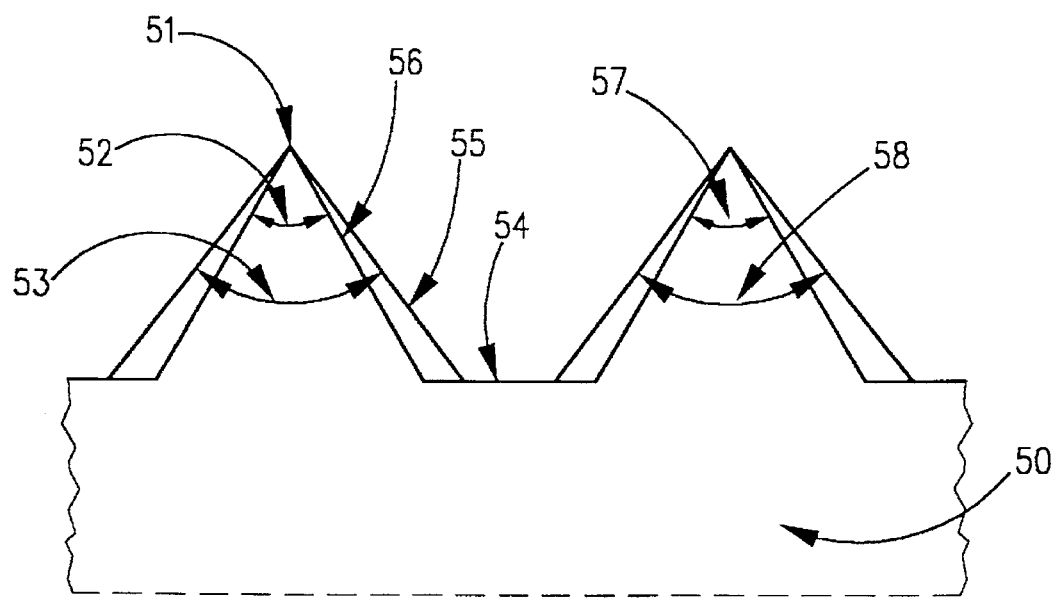
FIG. 8 shows threads with different flank angles.

FIG. 8 shows two superimposed portions of two externally threaded bodies which have different flank angles 52 and 53, respectively. The shank 50 of the externally threaded body has two helically extending ribs with symmetrical flanks 55 and 56 respectively; the character 54 points to the root of the threading. The externally threaded body with lower number in the set would comprise the flank 56 and the flank angle 52, whereas the externally threaded body with higher number in the set would be configured by the flank 55 and flank angle 53. If a screw fastener with the thread profile according to the externally threaded body of lower number in the set has lost the tight fit in a female threading, and due to other circumstances the repair mechanism cannot incorporate an increasing major diameter, then the following procedure according to this specially contoured set of externally threaded fasteners could be of interest. The repair mechanism comprises an increased flank angle 53 and an increase of thread ratio TE/TI, wherein TE stands for the area of the externally thread tooth 6 and TI denotes the area of the thread groove between two threads 7; thus, the previously widened internal threading comes again in tight contact with an appropriate screw fastener.

The flank angle need not be constant in all threads of one individual externally threaded body so that 52 and 57 may have different values than 53 and 58 may have respectively, if, for example, the left-handed screw thread belongs to the threaded start portion and the right-handed screw thread belongs to the threaded main portion.

Figure 9:
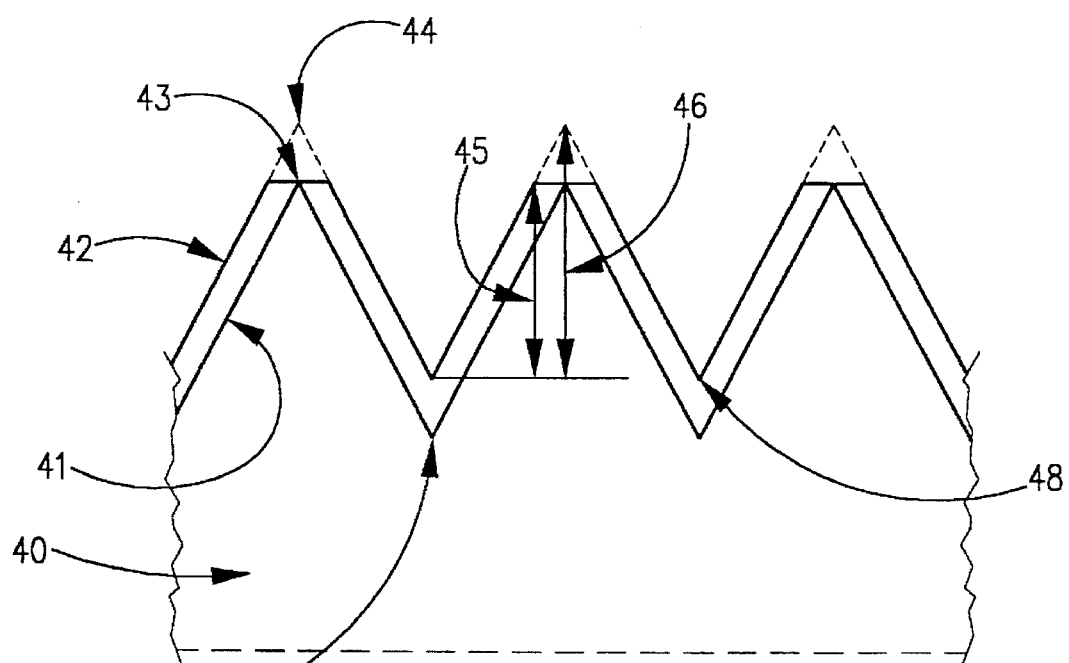
FIG. 9 shows threads with different minor diameters.

FIG. 9 shows two different repair mechanisms for loosened screw fasteners or damaged internal threadings. The shank 40 of the externally threaded body has two ribs with symmetrical flanks 41 and 42, respectively. The original thread configuration is determined by the flank 41, the crest 43 and the root 47. One repair mechanism uses a tapping body with the configuration according to the flank 42, the crest 43 and the root 48 with the consequence that the height 45 of the thread is reduced in comparison with the height 46 of the original threading, but the major diameter of the threading has not to be changed. The other repair procedure involves the cutting of a new internal threading with flank 42, crest 44 and root 48; in this case, the height of the thread is not reduced, but the major and minor diameters have been increased.

The selection of one specific of the different repair mechanisms for loosened screw fasteners according to the invention depends on the individual requirements of a construction.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A set of thread cutting taps each arranged to cut a final and usable female thread and each having a crest diameter and a root diameter, comprising a plurality of taps including a first tap having a first helical thread cutting ridge forming a first thread cutting thread and at least a second tap having a second helical thread cutting ridge forming a second thread cutting thread, each of said cutting threads having crest and root diameters at least one of which is smaller in said first tap than in said second tap, said cutting threads in all taps of the set having the same thread pitch independently of the differences between said diameters and said differences being sufficiently small to ensure that a female thread cut by said first tap is not damaged when such female thread is being enlarged by said second tap of the set.

2. The set of thread cutting taps of claim 1, wherein said taps of said set have at least incrementally increasing crest diameters.

3. The set of thread cutting taps of claim 1, wherein said taps have at least incrementally increasing root diameters.

4. The set of thread cutting taps of claim 1, wherein a connecting line through the crests of the cutting threads of different crest diameter bisects the screw threads.

5. The set of thread cutting taps of claim 1, wherein said at least one diameter of said first tap is smaller by at least 0.005 mm than the at least one diameter of said at least one second tap.

6. The set of thread cutting taps of claim 1, wherein each tap of the set has a thread cutting start portion with a start crest diameter and a thread cutting main portion with a main crest diameter larger than the respective start crest diameter, said at least one second tap having a start crest diameter which at least approximates the main crest diameter of said first tap.

7. The set of thread cutting taps of claim 6, wherein in a first portion of each tap the crest diameters of the threads continuously increase towards the respective main threaded portion.

8. The set of thread cutting taps of claim 7, comprising at least three thread cutting taps so dimensioned that each first thread of the start crest diameter of each higher number tap in the set corresponds to the main crest diameter of the next lower number in the set.

9. The set of thread cutting taps of claim 1, when used for bone tapping.

10. A set of externally threaded fasteners each having a thread crest diameter and a thread root diameter, said set comprising a first fastener having a first helical thread ridge forming a first thread and at least one second fastener having a second helical thread ridge forming a second thread, said first and second threads having at least one of said thread crest and root diameters that increase in at least one incremental step, said threads of all fasteners in the set having the same constant thread pitch independently of said incrementally increasing step in said at least one of said thread crest and root diameters.

11. A set of externally threaded fasteners of claim 10, wherein said incremental step of said at least one of said thread crest and root diameters is such that replacement of a fastener of a lower number in the set by a fastener with a next higher number in the set results in a tight fit in a female threading without damage to such female threading to be engaged by the thread of said fastener with said next higher number.

12. The set of externally threaded fasteners of claim 10, wherein said fasteners of said set have at least incrementally increasing crest diameters.

13. The set of externally threaded fasteners of claim 12, wherein said root diameters increase with at least one second incremental step that is larger than said at least one incremental step.

14. The set of externally threaded fasteners of claim 10, wherein said fasteners of said set have at least incrementally increasing root diameters.

15. The set of externally threaded fasteners of claim 10, wherein a connecting line through the crests of the threads of different crest diameters bisects the threads, said connecting line being an oblique line when said threads of different diameters are asymmetrical threads having non-symmetrical flanks.

16. The set of externally threaded fasteners of claim 10, wherein each incremental step is at least 0.05 mm.

17. The set of externally threaded fasteners of claim 10, wherein each fastener of the set has a start threaded portion and a main threaded portion, said start threaded portion having a crest diameter which is smaller than a main crest diameter of the respective main threaded portion, said at least one second fastener having a start crest diameter corresponding to said main crest diameter of said main threaded portion of said first fastener.

18. The set of externally threaded fasteners of claim 17, wherein in the start threaded portions the crest diameters increase continuously towards the respective main threaded portions so that the first thread at a tip of the respective fastener has the smallest crest diameter.

19. The set of externally threaded fasteners of claim 17, comprising at least three fasteners so dimensioned that each start crest diameter of each fastener having a higher number in the set corresponds to the main crest diameter of a next lower number fastener in the set.

20. The set of externally threaded fasteners of claim 17, wherein a fastener of lower number in the set functions as a cutting tap for a fastener of the next higher number in the set.

21. The set of externally threaded fasteners of claim 10, when used for bone fixation.

22. The combination of a first set of thread cutting taps and a corresponding second set of externally threaded fasteners, said first set comprising a plurality of thead cutting taps including at least a first tap having a first helical thread cutting ridge forming a first cutting thread, and a second tap having a second helical thread cutting ridge forming a second cutting thread, said cutting threads having crest diameters that increase in incremental steps from tap to tap starting with the first tap, said cutting threads of all taps in said first set having the same constant thread pitch independently of said incrementally increasing steps in said crest diameters and an increase in said incremental steps of said crest diameters in said taps is such that a female threading cut by a tap of a lower number in said first set is not damaged when such female threading is widened or repaired by a tap having a next higher number in said first set, said second set of externally threaded fasteners comprising a plurality of fasteners including at least a first fastener having a first helical thread ridge forming a first thread and a second fastener having a second helical thread ridge forming a second thread, said threads having thread crest diameters that increase in incremental steps from fastener to fastener in said second set starting with said first fastener, said threads of all fasteners in said second set having the same constant thread pitch independently of said incrementally increasing steps in said thread crest diameters of the fasteners and taps of both sets, each tap number in said first set corresponding to a certain fastener number in said second set in respect of the crest diameter so that the corresponding fastener number of said second set is a tight fit when engaging a female threading cut by the corresponding tap number of said first set, and a replacement of a fastener of lower number in said second set by a fastener with a next higher number in said second set results in a tight fit in a female threading without damage to such female threading to be engaged by said fastener with said next higher number in said second set for a tight fit.

23. The combination of claim 22, wherein the taps of said first set have tap crest diameters and tap root diameters and the fasteners of said second set have screw crest diameters and screw root diameters, said screw crest diameters being larger than said tap crest diameters and said screw root diameters being larger than said tap root diameters.

24. The combination of claim 23, wherein a difference between said crest diameters is within the range of about 0.05 to 0.2 mm and a difference between said root diameters is also within the range of about 0.05 to 0.2 mm.

* * * * *